United States Patent
Dostal et al.

(10) Patent No.: US 9,480,491 B1
(45) Date of Patent: *Nov. 1, 2016

(54) MEDICAL RETRIEVAL DEVICE

(71) Applicant: Annex Medical, Inc., Minnetonka, MN (US)

(72) Inventors: Daniel L. Dostal, Eden Prairie, MN (US); Eugene C. Karels, St. Louis Park, MN (US); Stuart J. Lind, Eden Prairie, MN (US)

(73) Assignee: Annex Medical, Inc., Minnetonka, MN (US)

( * ) Notice: Subject to any disclaimer, the term of this patent is extended or adjusted under 35 U.S.C. 154(b) by 45 days.

This patent is subject to a terminal disclaimer.

(21) Appl. No.: 14/329,308

(22) Filed: Jul. 11, 2014

Related U.S. Application Data

(63) Continuation of application No. 12/821,792, filed on Jun. 23, 2010, now Pat. No. 9,101,383, which is a continuation of application No. 10/831,986, filed on Apr. 26, 2004, now abandoned.

(60) Provisional application No. 60/466,024, filed on Apr. 25, 2003.

(51) Int. Cl.
*A61B 17/221* (2006.01)

(52) U.S. Cl.
CPC .................. *A61B 17/221* (2013.01)

(58) Field of Classification Search
CPC ............ A61B 17/00234; A61B 17/22; A61B 17/22031; A61B 17/221; A61B 17/32056; A61B 17/50; A61B 2017/00238; A61B 2017/00292; A61B 2017/00358; A61B 2017/22035; A61B 2017/2212
See application file for complete search history.

(56) References Cited

U.S. PATENT DOCUMENTS

| | | | |
|---|---|---|---|
| 651,395 A | | 6/1900 | Stapp |
| 1,054,960 A | * | 3/1913 | Butner .................. A61B 17/50 606/106 |

(Continued)

OTHER PUBLICATIONS

Application and File history for U.S. Appl. No. 11/094,894, filed Mar. 31, 2005. Inventors: Lind et al.

(Continued)

*Primary Examiner* — Ryan J Severson
(74) *Attorney, Agent, or Firm* — Patterson Thuente Pederson, P.A.

(57) ABSTRACT

A medical retrieval basket used for entrapping and extracting objects such as urinary and biliary calculi from the body comprising a handle assembly, a flexible shaft, and a basket. The basket comprises a plurality of outwardly disposed shape memory wires and is bulbous in shape at its distal end. Located at the intersection point of the wires at the distal end of the basket is a hub that restricts the degree of relative movement between the wires. This hub also serves to increase contact points with the object to be retrieved and to stabilize the orientation of the basket wires. The substantially tipless configuration of the distal end of the basket permits the basket to retrieve objects from difficult to reach locations and reduces tissue trauma caused by the basket tip. The basket wires have varying cross sectional shapes and sizes in different sections of the basket to optimize the performance to the needs of each section within the basket. The flexible shaft contains a drive wire that exhibits different flexibilities within the same strand of material by varied cross sectional shapes or diameters. This permits the distal section of the shaft to be more flexible, which reduces the possibility of the device shaft limiting the deflection of a flexible endoscope.

8 Claims, 13 Drawing Sheets

(56) References Cited

U.S. PATENT DOCUMENTS

| | | | |
|---|---|---|---|
| 1,677,671 A | 7/1928 | Councill | |
| 2,054,149 A * | 9/1936 | Wappler | A61B 17/32056 606/113 |
| 2,918,919 A | 12/1959 | Wallace | |
| 2,943,626 A | 7/1960 | Dormia | |
| 3,008,467 A | 11/1961 | Morris | |
| 3,080,867 A * | 3/1963 | Eichinger | A61B 17/12009 24/115 G |
| 3,162,214 A | 12/1964 | Bazinet | |
| 3,674,014 A | 7/1972 | Tillander | |
| 3,791,387 A | 2/1974 | Itoh | |
| 3,828,790 A | 8/1974 | Curtiss et al. | |
| 3,903,892 A | 9/1975 | Komiya | |
| 3,955,578 A | 5/1976 | Chamness et al. | |
| 4,046,149 A | 9/1977 | Komiya | |
| 4,046,150 A | 9/1977 | Schwartz et al. | |
| 4,198,960 A | 4/1980 | Utsugi | |
| 4,299,225 A | 11/1981 | Glassman | |
| 4,347,846 A | 9/1982 | Dormia | |
| 4,590,938 A | 5/1986 | Segura et al. | |
| 4,611,594 A | 9/1986 | Grayhack et al. | |
| 4,612,931 A | 9/1986 | Dormia | |
| 4,625,726 A | 12/1986 | Duthoy | |
| 4,633,871 A | 1/1987 | Shinozuka | |
| 4,655,219 A | 4/1987 | Petruzzi | |
| 4,685,895 A | 8/1987 | Hatten | |
| 4,691,705 A * | 9/1987 | Okada | A61B 17/221 606/127 |
| 4,790,812 A | 12/1988 | Hawkins, Jr. et al. | |
| 4,802,461 A | 2/1989 | Cho | |
| 4,807,626 A | 2/1989 | McGirr | |
| 4,815,476 A | 3/1989 | Clossick | |
| 4,927,426 A | 5/1990 | Dretler | |
| 4,955,384 A | 9/1990 | Taylor et al. | |
| 4,994,079 A | 2/1991 | Genese et al. | |
| 5,010,894 A * | 4/1991 | Edhag | A61N 1/3956 607/128 |
| 5,057,114 A | 10/1991 | Wittich et al. | |
| 5,064,428 A | 11/1991 | Cope et al. | |
| 5,066,295 A | 11/1991 | Kozak et al. | |
| 5,083,549 A | 1/1992 | Cho et al. | |
| 5,098,441 A * | 3/1992 | Wechler | A61B 17/221 606/113 |
| 5,146,928 A | 9/1992 | Esser | |
| 5,176,688 A | 1/1993 | Narayan et al. | |
| 5,201,741 A | 4/1993 | Dulebohn | |
| 5,325,845 A | 7/1994 | Adair | |
| 5,330,482 A | 7/1994 | Gibbs et al. | |
| 5,376,094 A | 12/1994 | Kline | |
| 5,381,782 A | 1/1995 | DeLaRama et al. | |
| 5,411,025 A * | 5/1995 | Webster, Jr. | A61B 5/0422 600/374 |
| 5,484,384 A | 1/1996 | Fearnot | |
| 5,496,330 A | 3/1996 | Bates et al. | |
| 5,499,981 A | 3/1996 | Kordis | |
| 5,549,661 A * | 8/1996 | Kordis | A61B 18/1492 600/374 |
| 5,573,520 A | 11/1996 | Schwartz et al. | |
| 5,573,530 A | 11/1996 | Fleury et al. | |
| 5,595,186 A | 1/1997 | Rubinstein et al. | |
| 5,647,870 A | 7/1997 | Kordis et al. | |
| 5,681,263 A | 10/1997 | Flesch | |
| 5,718,714 A | 2/1998 | Livneh | |
| 5,722,423 A | 3/1998 | Lind et al. | |
| 5,788,710 A | 8/1998 | Bates et al. | |
| 5,792,145 A | 8/1998 | Bates et al. | |
| 5,817,104 A | 10/1998 | Bilitz et al. | |
| 5,820,630 A | 10/1998 | Lind | |
| 5,833,632 A | 11/1998 | Jacobsen et al. | |
| 5,891,017 A | 4/1999 | Swindle et al. | |
| 5,911,739 A | 6/1999 | Kordis et al. | |
| 5,922,443 A | 7/1999 | Larsen et al. | |
| 5,931,830 A | 8/1999 | Jacobsen et al. | |
| 5,944,728 A | 8/1999 | Bates | |
| 5,957,932 A | 9/1999 | Bates et al. | |
| 5,989,266 A | 11/1999 | Foster | |
| 6,013,086 A * | 1/2000 | Ouchi | A61B 17/221 606/113 |
| 6,015,415 A | 1/2000 | Avellanet | |
| 6,053,934 A | 4/2000 | Andrews et al. | |
| 6,090,129 A | 7/2000 | Ouchi | |
| 6,093,196 A | 7/2000 | Okada | |
| 6,096,053 A | 8/2000 | Bates | |
| 6,152,932 A * | 11/2000 | Ternstrom | A61B 17/221 606/113 |
| 6,159,220 A | 12/2000 | Gobron et al. | |
| 6,168,603 B1 | 1/2001 | Leslie et al. | |
| 6,183,482 B1 | 2/2001 | Bates et al. | |
| 6,190,394 B1 | 2/2001 | Lind et al. | |
| 6,203,552 B1 | 3/2001 | Bagley et al. | |
| 6,216,044 B1 | 4/2001 | Kordis | |
| 6,224,612 B1 | 5/2001 | Bates et al. | |
| 6,235,026 B1 | 5/2001 | Smith | |
| 6,258,101 B1 | 7/2001 | Blake, III | |
| 6,273,876 B1 | 8/2001 | Klima et al. | |
| 6,280,451 B1 | 8/2001 | Bates et al. | |
| 6,299,612 B1 * | 10/2001 | Ouchi | A61B 18/14 606/113 |
| 6,302,895 B1 * | 10/2001 | Gobron | A61B 17/221 606/127 |
| 6,325,807 B1 | 12/2001 | Que | |
| 6,348,056 B1 | 2/2002 | Bates et al. | |
| 6,350,266 B1 | 2/2002 | White et al. | |
| 6,352,539 B1 | 3/2002 | Avellanet | |
| D457,955 S | 5/2002 | Bilitz | |
| 6,398,791 B1 | 6/2002 | Que et al. | |
| 6,419,679 B1 | 7/2002 | Dhindsa | |
| 6,458,145 B1 * | 10/2002 | Ravenscroft | A61B 17/221 606/127 |
| 6,494,885 B1 | 12/2002 | Dhindsa | |
| 6,500,182 B2 | 12/2002 | Foster | |
| 6,527,781 B2 | 3/2003 | Bates et al. | |
| 6,551,327 B1 | 4/2003 | Dhindsa | |
| 6,575,970 B2 | 6/2003 | Quick | |
| 6,585,734 B2 * | 7/2003 | Levinson | A61B 18/14 606/113 |
| 6,626,915 B2 | 9/2003 | Leveillee | |
| 6,652,537 B2 * | 11/2003 | Mercereau | A61B 17/221 606/113 |
| 6,676,668 B2 | 1/2004 | Mercereau et al. | |
| 6,682,493 B2 | 1/2004 | Mirigian | |
| 6,695,834 B2 | 2/2004 | Gellman et al. | |
| 6,740,030 B2 | 5/2004 | Martone et al. | |
| 6,743,237 B2 | 6/2004 | Dhindsa | |
| 6,752,811 B2 | 6/2004 | Chu et al. | |
| 6,921,397 B2 | 7/2005 | Corcoran et al. | |
| 7,101,379 B2 | 9/2006 | Gregory, Jr. et al. | |
| 7,413,563 B2 | 8/2008 | Corcoran et al. | |
| 7,559,934 B2 * | 7/2009 | Teague | A61B 17/221 606/113 |
| 8,021,372 B2 | 9/2011 | Bilitz | |
| 8,523,879 B1 | 9/2013 | Lind et al. | |
| 8,617,177 B2 * | 12/2013 | Uihlein | A61B 17/22031 606/113 |
| 8,870,895 B2 | 10/2014 | Bilitz | |
| 9,101,383 B1 | 8/2015 | Dostal et al. | |
| 2001/0001315 A1 | 5/2001 | Bates et al. | |
| 2002/0026202 A1 | 2/2002 | Honey et al. | |
| 2002/0068954 A1 | 6/2002 | Foster | |
| 2002/0091394 A1 * | 7/2002 | Reynolds | A61B 17/00234 606/127 |
| 2002/0133170 A1 | 9/2002 | Tsuruta | |
| 2002/0133171 A1 | 9/2002 | Que et al. | |
| 2003/0009176 A1 | 1/2003 | Bilitz | |
| 2003/0023247 A1 | 1/2003 | Lind et al. | |
| 2003/0055401 A1 | 3/2003 | Larson et al. | |
| 2003/0055423 A1 * | 3/2003 | Levinson | A61B 18/14 606/47 |
| 2003/0078593 A1 | 4/2003 | Bates et al. | |
| 2003/0088254 A1 | 5/2003 | Gregory, Jr. et al. | |
| 2003/0105480 A1 | 6/2003 | Wiener et al. | |

(56) References Cited

U.S. PATENT DOCUMENTS

| | | | |
|---|---|---|---|
| 2003/0109888 A1* | 6/2003 | Mercereau | A61B 17/221 606/127 |
| 2003/0109889 A1* | 6/2003 | Mercereau | A61B 17/221 606/127 |
| 2003/0120281 A1 | 6/2003 | Bates et al. | |
| 2003/0139750 A1 | 7/2003 | Shinozuka et al. | |
| 2003/0176859 A1* | 9/2003 | Levinson | A61B 18/14 606/47 |
| 2003/0225419 A1 | 12/2003 | Lippett et al. | |
| 2004/0106852 A1 | 6/2004 | Windheuser et al. | |
| 2004/0122444 A1 | 6/2004 | Gerard | |
| 2004/0133213 A1 | 7/2004 | Bagley et al. | |
| 2004/0199048 A1 | 10/2004 | Clayman et al. | |
| 2004/0199200 A1* | 10/2004 | Teague | A61B 17/221 606/200 |
| 2004/0215212 A1 | 10/2004 | Teague et al. | |
| 2005/0080400 A1 | 4/2005 | Corcoran et al. | |
| 2005/0125016 A1 | 6/2005 | Trerotola | |
| 2012/0095477 A1 | 4/2012 | Bilitz | |

OTHER PUBLICATIONS

Application and File history for U.S. Appl. No. 10/190,218, filed Jul. 5, 2002, now U.S. Pat. No. 8,021,372 issued Sep. 20, 2011. Inventors: Bilitz et al.

Application and File history for U.S. Appl. No. 13/236,031, filed Sep. 19, 2011, now U.S. Pat. No. 8,870,895 issued Oct. 28, 2010. Inventor: Bilitz.

Application and File history for U.S. Appl. No. 12/821,792, filed Jun. 23, 2010, now U.S. Pat. No. 9,101,383, issued Aug. 11, 2015, inventors Dostal et al.

Application and File history for U.S. Appl. No. 10/831,986, filed Apr. 26, 2004, inventors Dostal et al.

Application and File history for U.S. Appl. No. 14/329,308, filed Jul. 11, 2014, inventors Dostal et al.

Application and File history for U.S. Appl. No. 12/821,792, filed Jun. 23, 2010, issued as U.S. Pat. No. 9,101,383 on Aug. 11, 2015. Inventors: Dostal et al.

Application and File history for U.S. Appl. No. 13/987,137, filed Jul. 2, 2013. Inventors: Lind et al.

Application and File history for U.S. Appl. No. 14/804,108, filed Jul. 20, 2015, inventors Dostal et al.

* cited by examiner

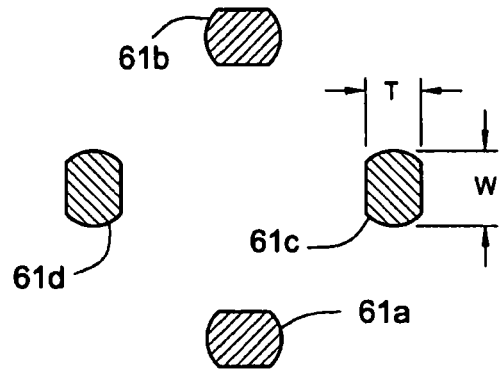
Fig.5b
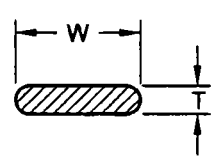
Fig.5a₁
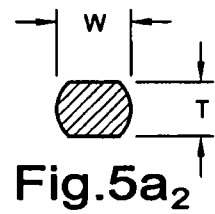
Fig.5a₂
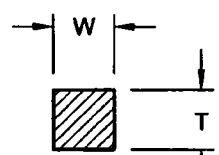
Fig.5b₁
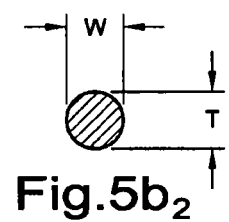
Fig.5b₂
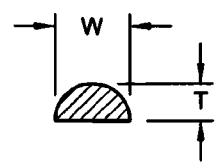
Fig.5c₁
Fig.5c₂

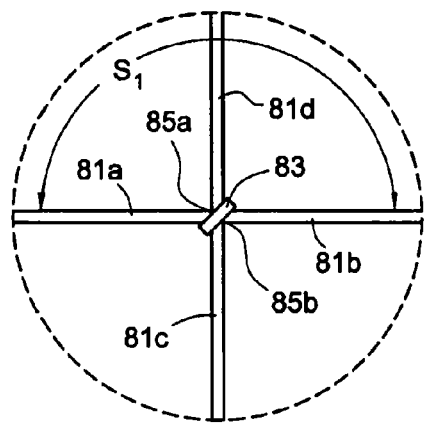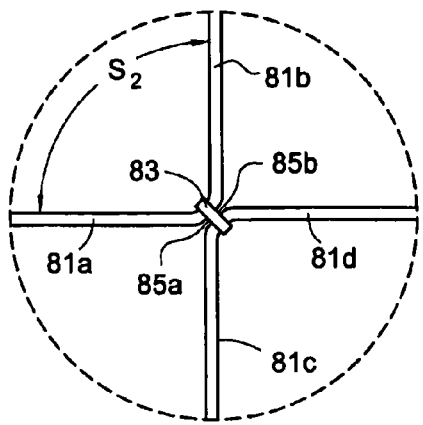
Fig.10a  Fig.10b
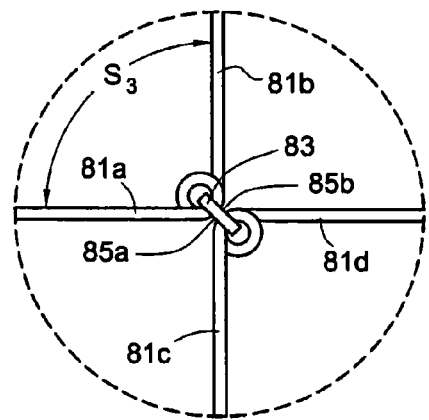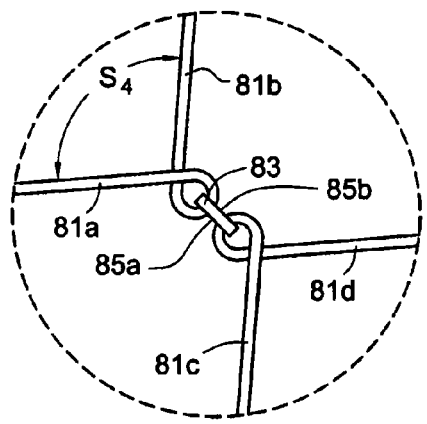
Fig.10c  Fig.10d

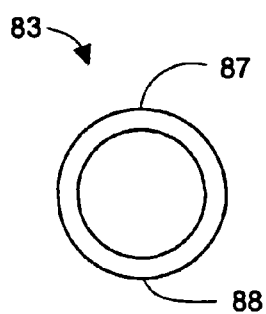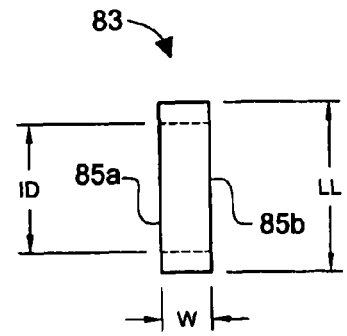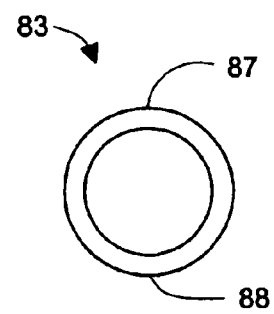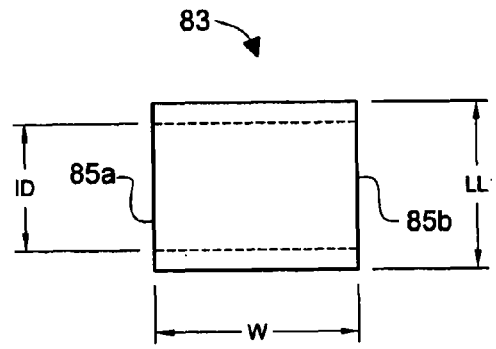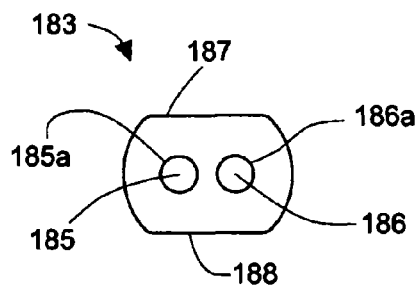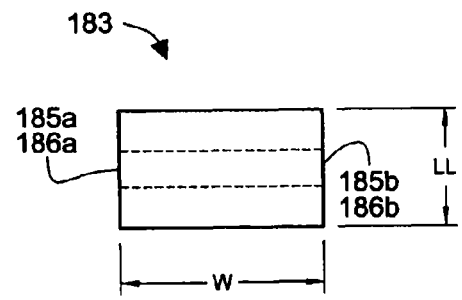

MEDICAL RETRIEVAL DEVICE

This application is a continuation of U.S. patent application Ser. No. 12/821,792, filed Jun. 23, 2010, which is a continuation of U.S. patent application Ser. No. 10/831,986, filed Apr. 26, 2004, which claims the benefit of U.S. Provisional Application No. 60/466,024, filed Apr. 25, 2003, the disclosures of each of which are incorporated herein by reference.

BACKGROUND OF THE INVENTION

This invention relates to medical retrieval devices for entrapping or removing objects from a body, particularly calculi from the urinary and biliary systems.

Medical instruments are currently in use that reduce the invasiveness and potential trauma previously associated with various medical procedures. One such procedure is the removal of objects, such as kidney stones and gallstones, from the body. Various medical retrieval devices are available which allow objects to be removed from the body without requiring major surgery. Typically, such instruments consist of 2 or more flexible elements that are joined at their proximal ends and may or may not be joined at their distal ends. The flexible elements, such as wires, are formed in the shape of a resiliently collapsible basket, cage, grasper, or other entrapping configuration. This basket is attached to a drive wire or actuation cable that passes through the lumen of a small diameter (typically 1 mm (3.0 Fr) or less) flexible sheath, which is usually greater than 50 cm in length. The sheath and drive wire comprise the shaft portion of the device. At the proximal end of the shaft, the sheath and drive wire are attached to a multi-part handle, normally constructed of thermoplastic materials, which can typically be operated by the user with a single hand. By manipulating the handle, the drive wire can be pulled back relative to the sheath, collapsing the basket as it retracts into the sheath. In this closed position, the sheath can be passed through the working channel of an endoscope to the proximity of the object to be removed within the patient's body. By manipulating the handle, which remains outside the endoscope and the patient's body, the basket is deployed from the end of the sheath, and expands to its open position. The device is then manipulated using the handle until the object becomes enclosed within the basket. This manipulation may include advancing, withdrawing and/or rotating the basket in order to get the object to pass between the flexible elements that comprise the basket. When the object has been successfully engaged within the basket, the basket is partially closed to secure the object within the basket wires, and the endoscope and the retrieval device containing the object are then simultaneously removed from the body.

Many different basket configurations are in use. When the basket wires are joined at their distal ends, this is often accomplished by securing the wires inside a small diameter tube, which typically has a length of 0.1-0.2 inches. However, such a tube has the disadvantage that it can cause trauma to body tissue because of its small diameter (typically 1 millimeter or less). In addition, it can be difficult or impossible with this basket configuration to retrieve objects that are positioned in difficult to reach locations, such as kidney stones located in a calyx of the kidney. Several prior art basket configurations have attempted to overcome these limitations. U.S. Pat. No. 4,590,938 (1986) to Segura et al. and U.S. Pat. No. 6,224,612 (2001) to Bates et al. disclose baskets with unsecured protrusions of the basket wires at the distal tip. These baskets have the disadvantage of protruding tips at the distal end that can make the retrieval of objects that are positioned in difficult to reach locations difficult or impossible. U.S. Pat. No. 5,057,114 (1991) to Wittich et al. and U.S. Pat. No. 5,064,428 (1991) to Cope et al. disclose baskets without extending tips. Wire loops in the basket are secured together at their distal ends using a urethane coated suture. These baskets have the disadvantage of questionable strength and stability. U.S. Pat. No. 5,989,266 (1999) to Foster et al. and U.S. Pat. No. 6,159,220 (2000) to Gobron et al. disclose baskets without extending tips. Intertwined basket wires or interconnecting loops made from the basket wires at the distal end of the basket are used to connect the basket wires together without using a protruding tip. While these baskets overcome the potential trauma and difficult retrieval location limitations caused by a protruding tip, some new limitations are introduced. In these configurations, stability of the basket wires previously provided by the protruding tip is lost. Without means to securely maintain the position of the basket wires relative to one another, stress from the surrounding anatomy or the object may force the basket wires radially out of their unrestricted configuration, possibly rendering the retrieval of the object more difficult or impossible. U.S. Pat. No. 6,527,781 (2003) to Bates et al. discloses a basket with a reversed cap that secures the basket wires at the distal end of the basket but extends proximally, into the center of the basket. This basket has the disadvantage of the cap being within the basket and possibly interfering with the object to be captured. All of the aforementioned patents are incorporated herein by reference. There is a need for an improved medical retrieval basket that does not have a protruding distal tip, but yet has a means for keeping the basket wires stable and securely positioned at the distal end of the basket.

In certain situations when a flexible endoscope is used, it may be necessary to articulate the tip of the endoscope significantly in order to reach the location of the object to be retrieved. This is accomplished using the active deflection mechanism of the endoscope. However, the shaft of the retrieval device, located in the endoscope's working channel, can in some situations limit the deflection of the endoscope. This can frequently be the case in difficult to reach locations, such as the lower poles of the kidney. U.S. Pat. No. 6,325,807 (2001) to Que and U.S. Pat. No. 6,398,791 (2002) to Que et al illustrate retrieval devices with a portion of the sheath near the distal end being more flexible than the rest of the sheath. These patents are incorporated herein by reference.

U.S. Pat. No. 6,190,394 (2001) to Lind et al illustrates a retrieval device with basket wires having differing sizes, cross sectional shapes and/or spacing. This patent is incorporated herein by reference.

SUMMARY OF THE INVENTION

A medical retrieval basket used for entrapping and extracting objects such as urinary and biliary calculi from the body comprising a handle assembly, a flexible shaft, and a basket. The basket comprises a plurality of outwardly disposed shape memory wires and is bulbous in shape at its distal end. Located at the intersection point of the wires at the distal end of the basket is a hub that restricts the degree of relative movement between the wires. This hub also serves to increase contact points with the object to be retrieved and to stabilize the orientation of the basket wires. The substantially tipless configuration of the distal end of the basket permits the basket to retrieve objects from difficult to reach locations and reduces tissue trauma caused by the basket tip. The basket wires have varying cross sectional shapes and sizes in different sections of the basket to optimize the performance to the needs of each section within the basket. The flexible shaft contains a drive wire that exhibits different flexibilities within the same strand of material by varied cross sectional shapes or diameters. This permits the distal section of the shaft to be more flexible, which reduces the possibility of the device shaft limiting the deflection of a flexible endoscope.

An object and advantage of preferred embodiments of the invention is to provide a medical retrieval device with basket wires joined at the distal end having a configuration that enables the basket to retrieve objects that are positioned in difficult to reach locations, such as kidney stones located in a calyx of the kidney.

Another object and advantage of the preferred embodiments is to provide a medical retrieval device with a distal area that reduces the possibility of trauma to body tissue.

A further object and advantage of the preferred embodiments is to provide a medical retrieval device of the type described herein with increased contact points to assist in retaining the retrieved objects during removal.

Another object and advantage of the preferred embodiments is to provide a medical retrieval device of the type described herein that has a mechanism for restricting the degree of relative movement between the basket wires.

An object and advantage of the preferred embodiments is to provide a medical retrieval device of the type described herein that uses basket wire cross sections and distal end attachment configurations that optimize the performance of the different sections of the basket to facilitate the efficient capture of objects.

Another object and advantage of the preferred embodiments is to provide a medical retrieval device of the type described herein that has a shaft that is flexible at its distal end so as not to restrict the deflection of a flexible endoscope.

An object and advantage of preferred embodiments of the invention is to provide a medical retrieval device with a mechanism for precisely rotating the basket that is independent of the actuation mechanism.

Further objects and advantages of preferred embodiments of the medical retrieval device described herein are that such preferred embodiments are safe, reliable, and easy to use. Still further objects and advantages will become apparent from a consideration of the ensuing description and drawings.

BRIEF DESCRIPTION OF THE DRAWINGS

FIG. 4b is an end view of FIG. 4a.

Figure 5:
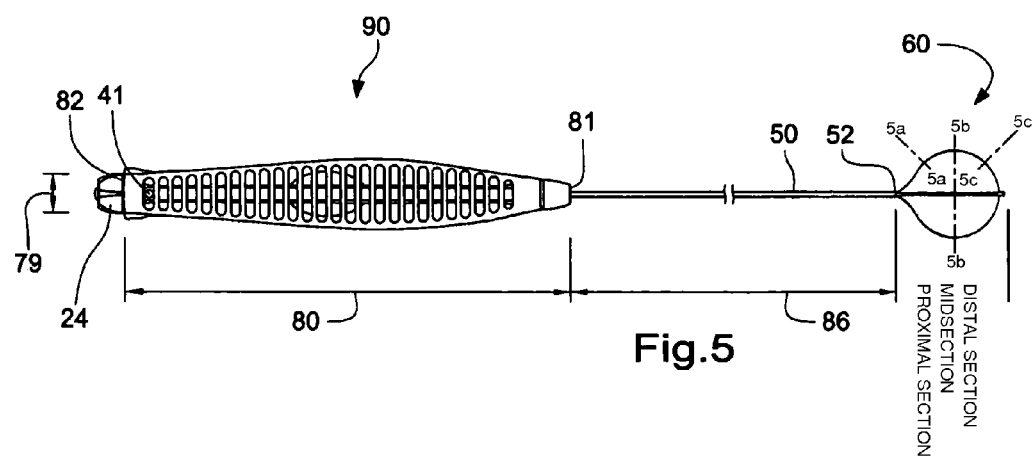
FIG. 5 is a bottom view of FIG. 1 and also shows the proximal, mid, and distal sections of the basket.

FIGS. $5a_1$, $5b_1$, and $5c_1$ are cross-sectional views of a single wire taken on lines 5a-5a, 5b-5b and 5c-5c, respectively, in FIG. 5.

FIGS. $5a_2$, $5b_2$, and $5c_2$ are cross-sectional views of a single wire of an alternate embodiment taken on lines 5a-5a, 5b-5b and 5c-5c, respectively, in FIG. 5.

FIG. 5b is a cross-sectional view of taken on line 5b-5b in FIG. 5.

Figure 3:
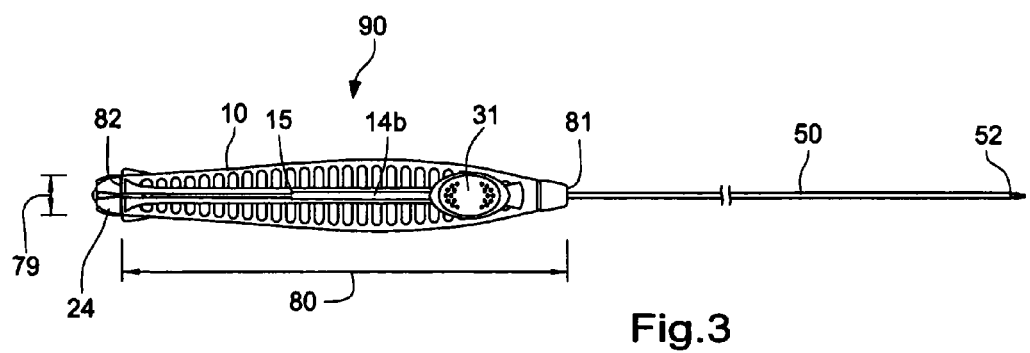
FIG. 3 is a top view of FIG. 1 showing the basket in the retracted or closed position.
Figure 4:
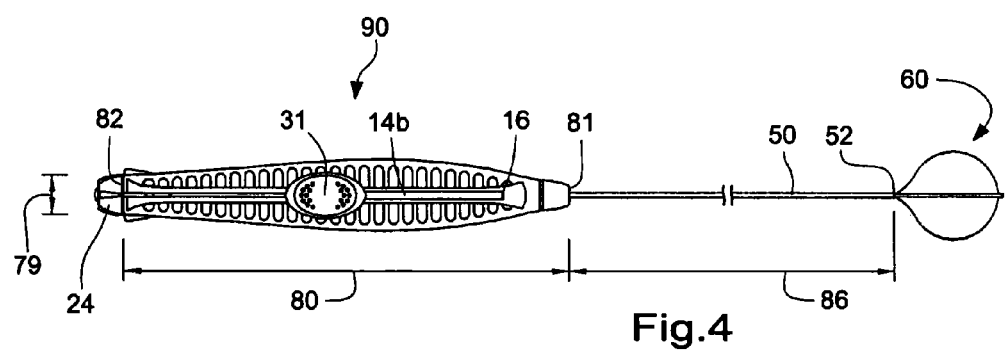
FIG. 4 is a top view of FIG. 1 showing the basket in the extended or open position.
Figure 3A:
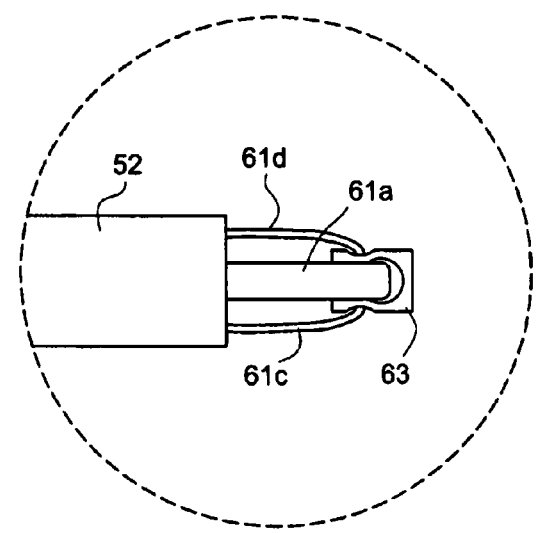
FIG. 3a is an enlarged view of the distal end of FIG. 3 showing the basket in the retracted or closed position.
Figure 4A:
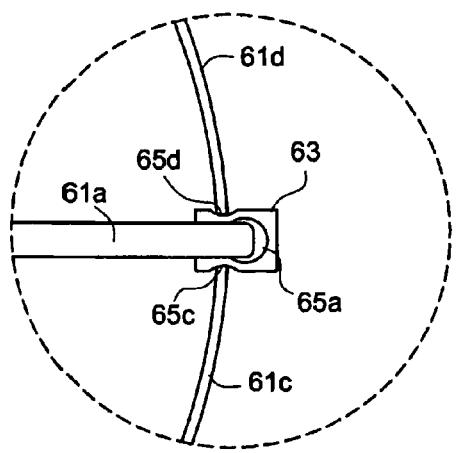
FIG. 4a is an enlarged view of the distal end of FIG. 4 showing the intersecting area of the basket wires.
Figure 4B:
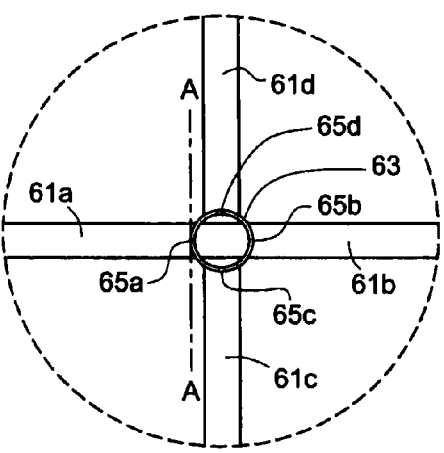
Figures 6A, 6B:
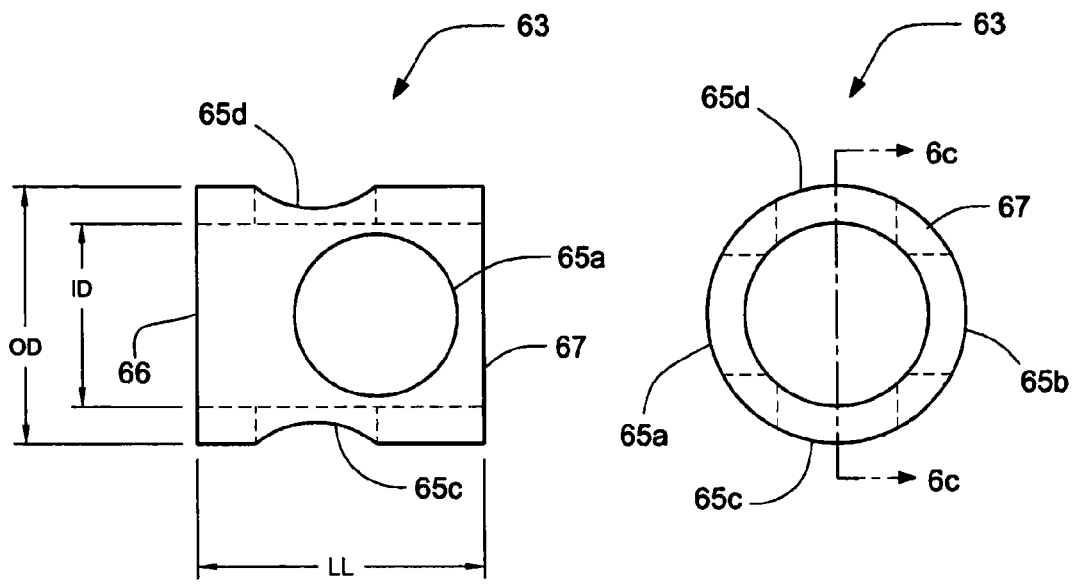

FIG. 6a is a side view of the hub shown in FIGS. 3a, 4a and 4b.

FIG. 6b is end view of FIG. 6a.

Figure 6C:
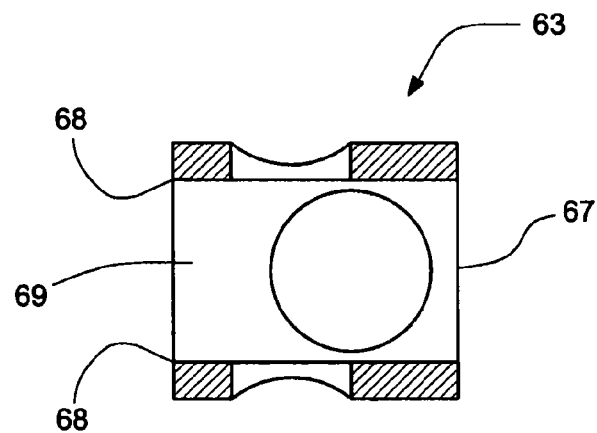

FIG. 6c is a cross-sectional view taken on line 6c-6c in FIG. 6b.

Figure 7:
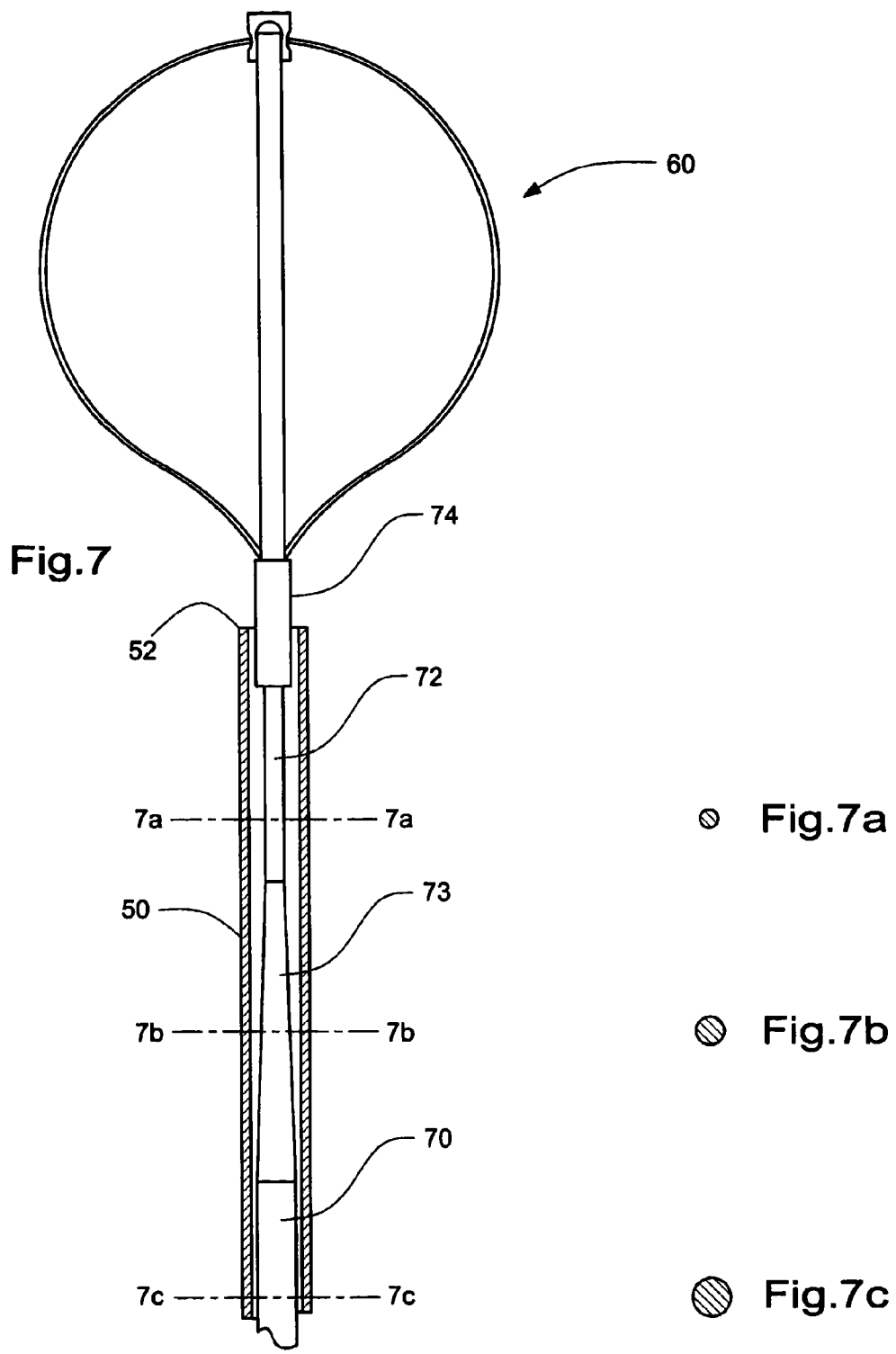

FIG. 7 shows a view in perspective and partly in section of the distal portion of FIG. 4.

FIGS. 7a, 7b, and 7c are cross-sectional views taken on lines 7a-7a, 7b-7b, and 7c-7c, respectively, in FIG. 7, but showing the cross-section of only the drive wire 70 according to this invention.

Figure 8:
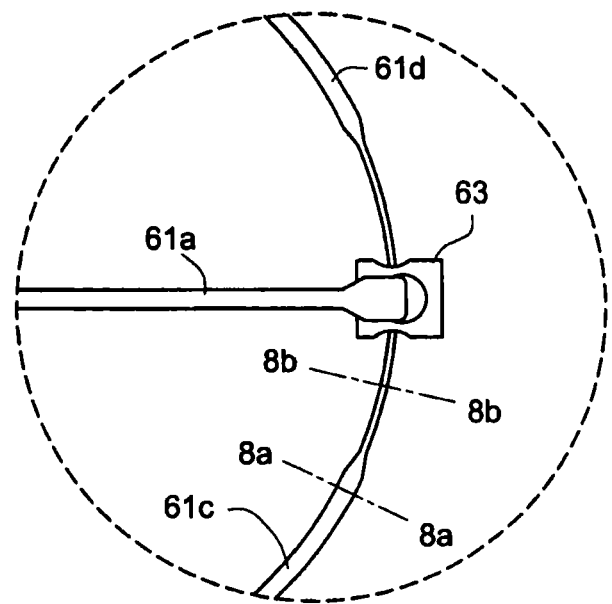

FIG. 8 is a similar view as FIG. 4a but showing another embodiment in which the wire is round but flattened at the very distal end of the basket.

Figure 8A:
Figure 8B:
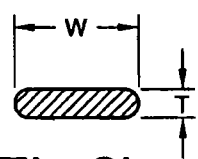

FIGS. 8a and 8b are cross-sectional views taken on lines 8a-8a and 8b-8b, respectively, in FIG. 8.

Figure 9:
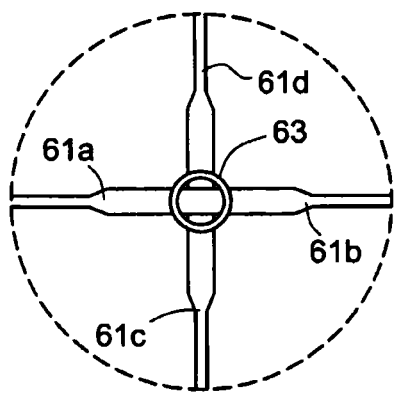

FIG. 9 is an end view of FIG. 8.

FIG. 10a is an end view of the intersecting area similar to FIG. 4b but showing an alternate embodiment.

FIG. 10b is an end view of the intersecting area similar to FIG. 10a showing another embodiment.

FIG. 10c is an end view of the intersecting area similar to FIGS. 10a and 10b showing another embodiment.

FIG. 10d is an end view of the intersecting area similar to FIGS. 10a, 10b, and 10c showing another embodiment.

FIG. 11a is an enlarged view of the hub shown FIGS. 10a-10d.

FIG. 11b is a side view of FIG. 11a.

FIGS. 11c and 11d are end and side views of an elongated hub.

FIGS. 11e and 11f are end and side views of another embodiment of the hub.

Figure 12A:
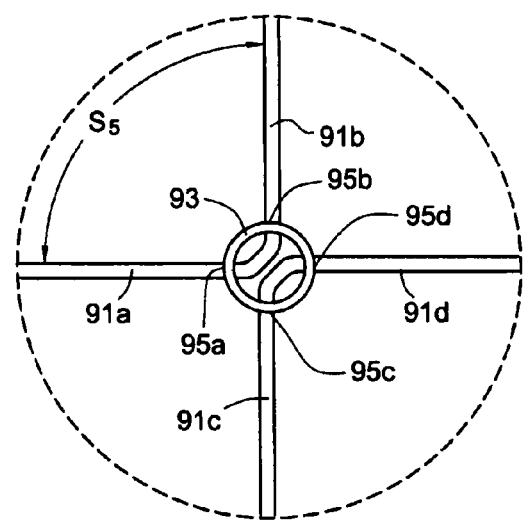

FIG. 12a is an end view of the intersecting area similar to FIG. 4b but showing an alternate embodiment.

Figure 12B:
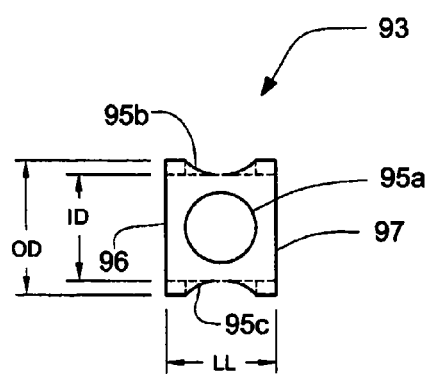

FIG. 12b is an enlarged view of the hub shown FIG. 12a.

Figure 12C:
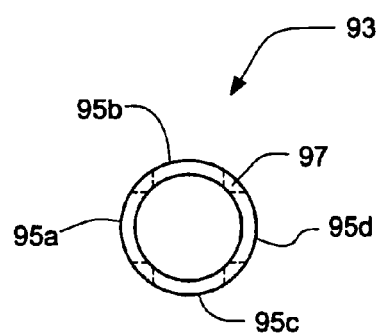

FIG. 12c is an end view of FIG. 12b.

Figure 13A:
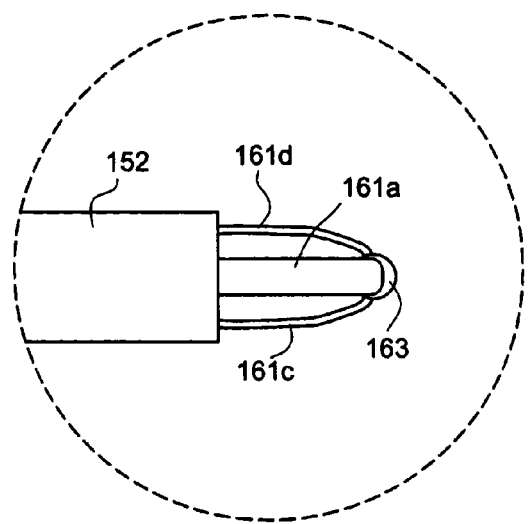

FIG. 13a is an enlarged view of the distal end of FIG. 3 showing the basket in the retracted or closed position with an alternate embodiment of the invention.

Figure 13B:
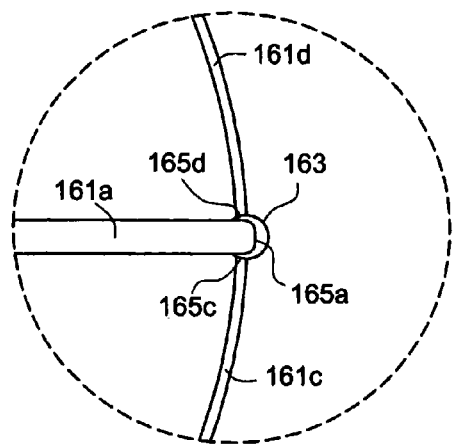

FIG. 13b is an enlarged view of the distal end of FIG. 4 showing the hub and intersecting area of the basket wires with an alternate embodiment of the invention.

Figure 13C:
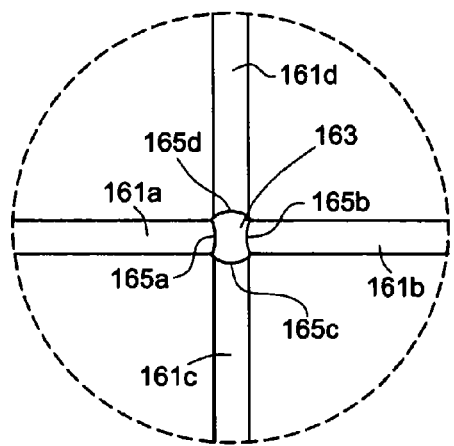

FIG. 13c is an end view of FIG. 13b.

Figure 14A:
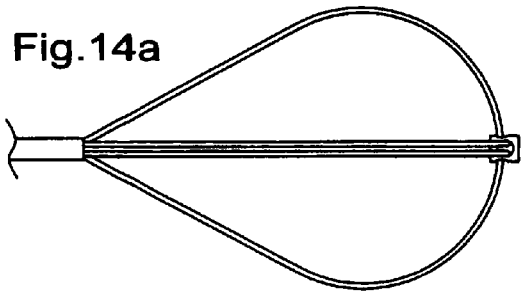

FIG. 14a shows a view in perspective of the invention in another embodiment.

Figure 14B:
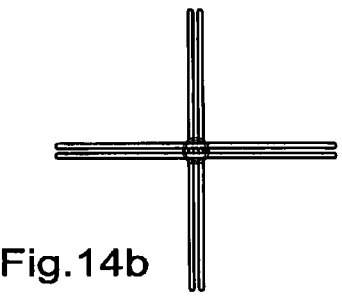

FIG. 14b is an end view of FIG. 14a.

Figure 14C:
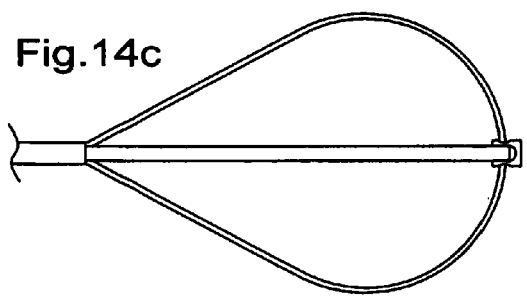

FIG. 14c shows a view in perspective of the invention in another embodiment.

Figure 14D:
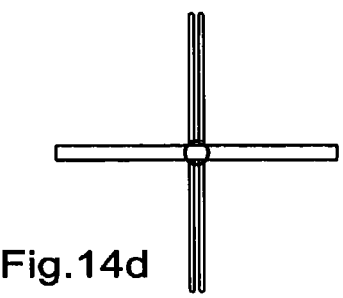

FIG. 14d is an end view of FIG. 14c.

Figure 14E:
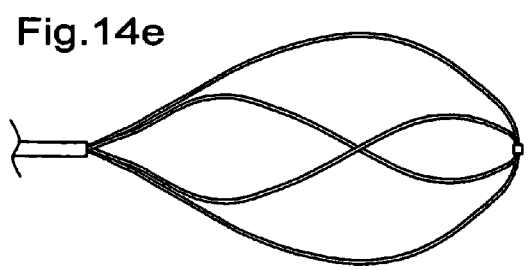

FIG. 14e shows a view in perspective of the invention in another embodiment.

Figure 14F:
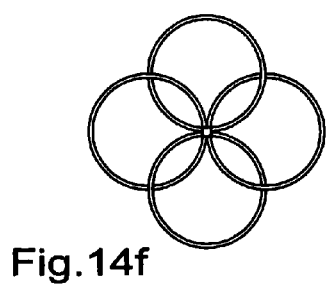

FIG. 14f is an end view of FIG. 14e.

DETAILED DESCRIPTION OF PREFERRED EMBODIMENTS

FIGS. 1 to 7c show some of the many possible embodiments of the invention. A medical retrieval device has a handle assembly 90, which has a longitudinal axis 11. Handle assembly 90 is comprised of an elongate handle base 10, a rotation means or spinner 20, a sliding portion or thumb slide 30, and a pin 40, all of which are preferably constructed of thermoplastic materials. Handle base 10 has a proximal end 82, a distal end 81, and a length 80, which is between 5 and 20 cm. Handle base 10 is essentially hollow along longitudinal or long axis 11, with an internal bore and an opening 12 at distal end 81. A longitudinal slot having a narrow portion 14a and a wide portion 14b is located on the top surface of handle base 10. Wide portion 14b has a proximal end 15 and a distal end 16. Narrow portion 14a extends from proximal end 82 of handle base 10 to wide portion 14b. Distal end 16 of wide portion 14b is located proximal to distal end 81 of handle base 10.

Thumb slide 30 has a thumb pad 31 and a guide portion configured as a fin 33, which has an upper portion 33a and a lower portion 33b. The width of upper portion 33a of fin 33 is wider than the width of narrow portion of slot 14a and narrower than the width of wide portion of slot 14b. The width of lower portion 33b of fin 33 is wider than the width of wide portion of slot 14b. A through hole 32 passes through lower portion 33b of fin 33 longitudinally. Thumb slide 30 is located on handle base 10 with upper portion 33a of fin 33 located within wide portion of slot 14b and lower portion 33b of fin 33 located within the hollow portion of handle base 10 below wide portion 14b. With thumb slide 30 engaged with wide portion of slot 14b in this manner, thumb slide 30 can be readily moved so that fin 33 is in any position within wide portion of slot 14b between proximal end 15 and distal end 16, but cannot inadvertently be removed vertically or longitudinally from wide portion of slot 14b in handle base 10. Handle base 10 also limits rotational movement of thumb slide 30. The total length of longitudinal travel of thumb slide 30 relative to handle base 10 is preferably 5 cm or less. Thumb pad 31 is located between proximal end 82 and distal end 81 of handle base 10. The actuation of thumb pad 31 overlaps the area between proximal end 82 and distal end 81 of handle base 10. A tube or sheath 50 has a proximal end 51, a distal end 52, and may be constructed of polyimide, PTFE, or other flexible material or combination of materials, and has a lumen through its entire length. Sheath 50 has a working length 86 that is preferably between 65 and 125 cm, and the diameter of sheath 50 is preferably approximately 1 mm or less. Sheath 50 passes through opening 12, which is substantially larger in diameter than sheath 50. Proximal end 51 of sheath 50 passes into through hole 32 in thumb slide 30 and is secured to thumb slide 30 using adhesive or other means.

Spinner 20 has a knob portion 24 and a cylindrical portion 23 that has a groove 22 extending around its circumference. Spinner 20 is located at proximal end 82 of handle base 10, with cylindrical portion 23 located within the hollow space of handle base 10 and knob portion 24 of spinner 20 located at proximal end 82 of handle base 10. A hole 21 is located in cylindrical portion 23 along longitudinal axis 11, and extends part way through spinner 20. Knob portion 24 of spinner 20 is axially positioned, and has a diameter 79 that is preferably 1.5 cm or less. Pin 40 has a head 41 and a tip 42. Pin 40 fits snugly into a hole in handle base 10, and tip 42 of pin 40 fits into groove 22. The length of pin 40 is such that when pin 40 is fully seated in the hole with head 41 contacting handle base 10, tip 42 extends into groove 22 in spinner 20, but does not fit snugly in groove 22. Thus spinner 20 is rotatably attached to handle base 10. This configuration limits the longitudinal movement of spinner 20 relative to handle base 10, but permits spinner 20 to rotate freely about longitudinal axis 11 relative to handle base 10. Handle assembly 90 has a longitudinally stationary portion that comprises handle base 10, spinner 20, and pin 40.

A drive wire 70 has a proximal end 71 and a distal end 72. Referring to FIGS. 7 to 7c, distal end 72 has a smaller diameter than the balance of drive wire 70. The length of this section is preferably between 0 and 10 inches. Between the smaller diameter distal end 72 and the larger diameter portion of drive wire 70 is a tapered section 73. Drive wire 70 may be constructed or formed of a shape memory material, such as nickel titanium alloy, stainless steel, or another material with similar properties. The smaller diameter distal end 72 and the tapered section 73 may be made by centerless grinding or other means. The configuration results in drive wire 70, and thus the shaft consisting of drive wire 70 within sheath 50, having a distal section that is more flexible than the remainder of the shaft. Alternatively, this flexibility could be attained by having some or all of the basket wires continue proximally from the basket and replace a section of the distal end of the drive wire. Referring again to FIGS. 1 to 5, drive wire 70 slidably extends through the lumen of sheath 50, with proximal end 71 of drive wire 70 extending past proximal end 51 of sheath 50. Proximal end 71 of drive wire 70 fits into hole 21 in spinner 20 and is secured using adhesive or other means. Sheath 50 is longitudinally movable relative to drive wire 70.

Figure 4C:
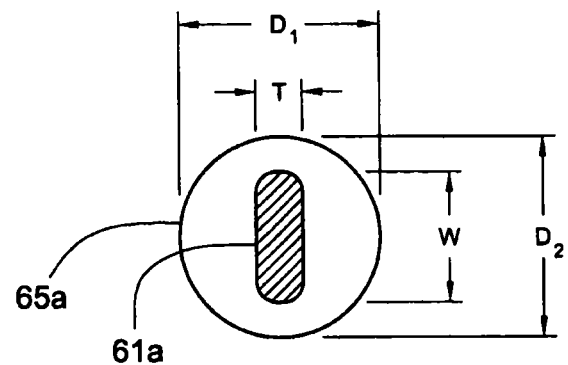
FIG. 4c is a cross-sectional view taken on line A-A in FIG. 4b showing the perimeter of the port and the wire cross-section.
Figure 4D:
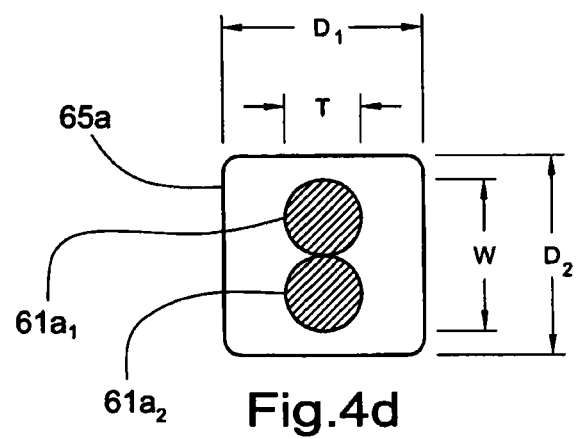
FIG. 4d is similar to FIG. 4c but showing an alternate embodiment.
Figure 4E:
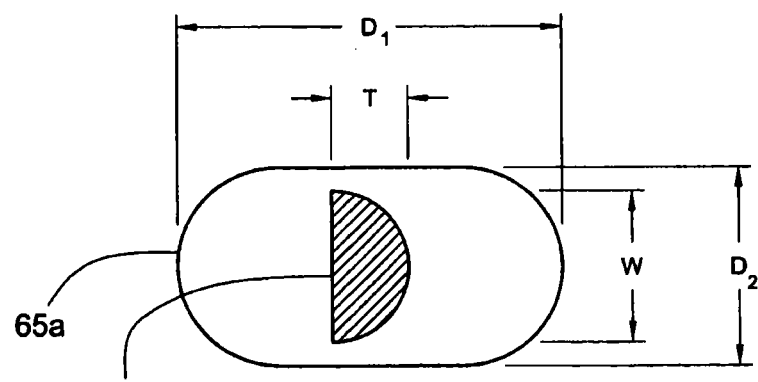
FIG. 4e is similar to FIG. 4c but showing an alternate embodiment.

An object entrapping assembly or basket 60 is located distal to drive wire distal end 72. Basket 60 consists of a plurality of flexible elements or wires 61a to 61d that are outwardly disposed about longitudinal axis 11 to form a space for entrapping objects when open. Basket wires 61a to 61d may be constructed or formed of a shape memory material, such as nickel titanium alloy (for example, nitinol), stainless steel, or another material with similar properties, and have a largest cross-sectional dimension that is typically between 0.005 and 0.015 inches. In the embodiment shown, there are four basket wires. Basket wires 61a and 61b are formed of a continuous piece of wire, and basket wires 61c and 61d are formed of a second continuous strand or piece of wire. Both ends of each of the two continuous strands of wire are attached to drive wire distal end 72, with the remainder of the two wires forming two loops that are perpendicular to each other, and intersect at the distal end of basket 60. Referring to FIGS. 4a and 4b, these two loops are connected at their distal intersecting area by means of a wire collector or hub 63, which is disposed at the distal end of basket 60. In certain embodiments, shown in FIGS. 6a to 6c, hub 63 is in the shape of a hollow ring having an outside diameter OD, an inside diameter ID, and a cavity 69. Hub 63 is constructed of a rigid material such as stainless steel, nickel titanium alloy, or a material with similar properties; or of a flexible material, such as rubberized thermoplastic, silicone, or a material with similar properties. Hub 63 may be made from hypodermic tubing, or may be formed by machining, extruding, molding, casting or other processes known in the art. Hub 63 may be a substantially rigid body or a substantially flexible body. Hub 63 has a proximal end 66 and a distal end 67. At proximal end 66, inside diameter ID and cavity 69 form an inwardly disposed contact element 68, which provides increased contact points for a generally spherical object to assist in retaining the object. Hub 63 has a plurality of ports, passages, or holes 65a-65d passing through it radially that are spaced approximately 90° to each other. These radially disposed holes may be made by machining, laser cutting, punching, or other means known in the art. Holes 65a-65d act as receiving means for the basket wires, and may be sized to provide a friction fit, or binding means, to secure the basket wires, or may be sized to allow the wires greater freedom of movement. Two holes 65a and 65b that are opposite each other are located closer to distal end 67 of hub 63, and the other two opposite holes 65c and 65d are located closer to proximal end 66 of hub 63. In preferred embodiments, hub 63 has a longitudinal length LL of 0.040 inches or less, but preferably 0.020 inches or less. The wire that forms basket wires 61a and 61b passes through the set of opposite holes 65a and 65b located closer to the distal end 67, and the wire that forms basket wires 61c and 61d passes through the set of opposite holes 65c and 65d located closer to the proximal end 66. Thus basket wires 61a to 61d extend from hub 63 in an orientation that is generally transverse to longitudinal axis 11 when basket 60 is in the open position. Hub 63 may or may not be secured to basket wires 61a to 61d using adhesive, solder, or another hardenable material, or by laser welding or other binding means. FIG. 4c shows the cross-sectional view of basket wire 61a at the point where it engages hole 65a. Basket wire 61a, which has a substantially rectangular cross-section, has a thickness T and a width W. In certain embodiments, the width to thickness ratio is greater than 1.5:1.0. Hole 65a has a first opening dimension $D_1$, which is in the same orientation as thickness T, and a second opening dimension $D_2$, which is in the same orientation as width W. In this embodiment, opening dimension $D_1$ is substantially greater than thickness T, and opening dimension $D_2$ is substantially greater than width W. In preferred embodiments, the opening size or area of the holes is at least 10% greater than the wire cross-sectional size or area, preferably it is approximately 50% greater or more. In these embodiments, the holes act as hinging means for the basket wires as the basket opens and closes. In other embodiments, one or both of opening dimensions $D_1$ and $D_2$ may be substantially equal to thickness T and width W, respectively. FIG. 4d shows another possible hole and basket wire configuration. In this example, hole 65a is essentially square in shape, and has two basket wires $61a_1$ and $61a_2$, which have circular cross-sections, engaged within. Wires $61a_1$ and $61a_2$ are closely spaced so that the two wires have a combined width W equal to the sum of the widths of the two wires, and a thickness T that is the same as the individual thickness of one wire. In this embodiment, opening dimension $D_1$ is substantially greater than thickness T, and opening dimension $D_2$ is substantially greater than width W. In other embodiments, one or both of opening dimensions $D_1$ and $D_2$ may be substantially equal to thickness T and width W, respectively. FIG. 4e shows yet another possible hole and basket wire configuration. Basket wire 61a, which has a semicircular cross-section, has a thickness T and a width W. Hole 65a, which has a substantially oval shape, has a first opening dimension $D_1$, which is in the same orientation as thickness T, and a second opening dimension $D_2$, which is in the same orientation as width W. In this embodiment, opening dimension $D_1$ is substantially greater than thickness T, and opening dimension $D_2$ is substantially greater than width W. In other embodiments, one or both of opening dimensions $D_1$ and $D_2$ may be substantially equal to thickness T and width W, respectively. Many other combinations of wire cross-sections and hole shapes are possible, and for each combination, the holes may be sized in one or both dimensions so as to provide a friction fit, or binding means, to secure and restrict the basket wires, or may be sized to allow the wires greater freedom of movement.

It can be seen that hub 63 provides a means for securing the basket wires at the distal end of the basket in such a manner that the basket is substantially tipless. Additionally, the basket wires are substantially non-parallel to, and preferably perpendicular to, the longitudinal axis at the distal end of the basket when the basket is in the open position. Many other embodiments of the hub are within the scope of the present invention. For example, holes 65a-65d may be located differently on the hub, such as all equidistant from the ends of the hub. The holes could be spaced at differing angles to each other, for example, to form a basket with differing spacing between basket wires, as described in U.S. Pat. No. 6,190,394 (2001) to Lind et al. Some or all of the holes may be located such that they are not completely surrounded by the hub material, but partially intersect one end of the hub, in the form of a notch. Holes 65a-65d may be circular in shape, or may be oval, rectangular, square, triangular, or other suitable shapes. Additionally, the different holes in the hub may differ from one another in size and shape. In another embodiment, hub 63 could be made of a solid rather than a ring-shaped piece. In this case, cavity 69 and contact element 68 may or may not be present at proximal end 66. Hub 63 could also have a shape that is not generally cylindrical.

Basket wires 61a to 61d are formed about longitudinal axis 11 by means known in the art to the desired basket shape and size. The basket shape may be such that opposing basket wires 61a and 61b are substantially planar and opposing basket wires 61c and 61d are substantially planar, or the basket wires may be in a substantially non-planar configuration, such as to form, for example, a basket having a helical configuration. Basket 60 has a generally bulbous form at its distal end, which is defined by hub 63. In some embodiments, the distal portion of the basket is substantially hemispherical in shape. For simplicity of understanding, the drawings are limited to baskets consisting of four wires. Other numbers are within the scope of the present invention. For example, the basket could consist of six wires. In this case, the hub would have six holes, spaced approximately 60° to each other. While it is preferred that opposing basket wires be formed of a continuous piece of wire, it is also possible that each basket wire be made from a separate piece of wire. In this case, the wires would terminate within the hub and be joined to each other within the hub and/or to the hub by means of soldering, laser welding, crimping, adhesive bonding, by deforming or enlarging the ends of the wires so that they will not pass through the holes, or by other means. Such termination of wires within the hub would be necessary for a basket consisting of an odd number of basket wires.

In certain embodiments, shown in FIG. 5b, basket wires 61a to 61d are constructed of round wire that has been slightly flattened to a thickness T and a width W. In this embodiment, the ratio of width to thickness dimensions is approximately 1.1:1.0 to 1.5:1.0. In other embodiments, wires flattened with width to thickness ratios greater than 1.5:1.0 (such as in FIG. 4c) also have significant benefit.

In other embodiments, a single basket wire may have different cross-sections in different sections of the basket. The advantage to this is to give basket wire in different sections of the basket different characteristics to enhance the overall performance of the basket. For example, it would be advantageous if the basket wires in the proximal section of the basket enhanced the stability and radial force of the basket, while the basket wires in the distal section of the basket provided maximum flexibility for capturing calyceal stones and reduced the stress to the basket wires in the closed position. One possible example of this is shown in FIGS. 5, $5a_1$, $5b_1$, and $5c_1$. In this example, the basket wire is flattened in the proximal section of the basket (FIG. $5a_1$), square in the midsection of the basket (FIG. $5b_1$), and hemispherical in the distal section of the basket (FIG. $5c_1$). Such a wire could be made by flattening one end and pressing the other end in a hydraulic press using appropriate fixtures to attain the desired cross-sectional shapes. A second possible example of multiple cross-section basket wires is shown in FIGS. 5, $5a_2$, $5b_2$ and $5c_2$. In this example, the basket wire is flattened slightly in the proximal section of the basket (FIG. $5a_2$), round in the midsection of the basket (FIG. $5b_2$), and round but with smaller diameter in the distal section of the basket (FIG. $5c_2$). Such a wire could be made by flattening one end and centerless grinding the other end.

In another embodiment, shown in FIGS. 8 to 9, a section of the basket wires at the distal end of the basket is flattened or has a reduced radial dimension. For example, if the basket wires are constructed of round wires, as shown in FIG. 8a, a section of the basket wires within and immediately surrounding hub 63 are flattened to have a width W that is greater than thickness T, with typical width to thickness ratios of 1.1:1 to 5:1. This serves to reduce the amount of stress to the basket wires when the basket is in the closed position. In another embodiment, the entire length of the basket wires may be rolled, shape drawn, or flattened, with typical width to thickness ratios of 1.1:1 to 5:1. In another embodiment, the basket wires may be round. In yet another embodiment, the basket wires may consist of several wires twisted together to form a strand.

Referring to FIG. 7, the basket wires and drive wire distal end 72 are joined within a connecting tube 74, which is constructed of hypodermic tubing made of stainless steel, nickel titanium alloy, or another material. The wires are secured within the tube by joining means known in the art such as soldering, crimping, laser welding, swaging, interference fit, adhesive bonding, or other known joining means. Alternatively, part or all of drive wire 70 may be constructed of the same continuous pieces of wire that form basket wires 61a to 61d, which may or may not be twisted together to form a strand in the drive wire section. In this case, a connecting tube would not be needed, but a tube or other securing means may be used to define the proximal end of basket 60.

Figure 1:
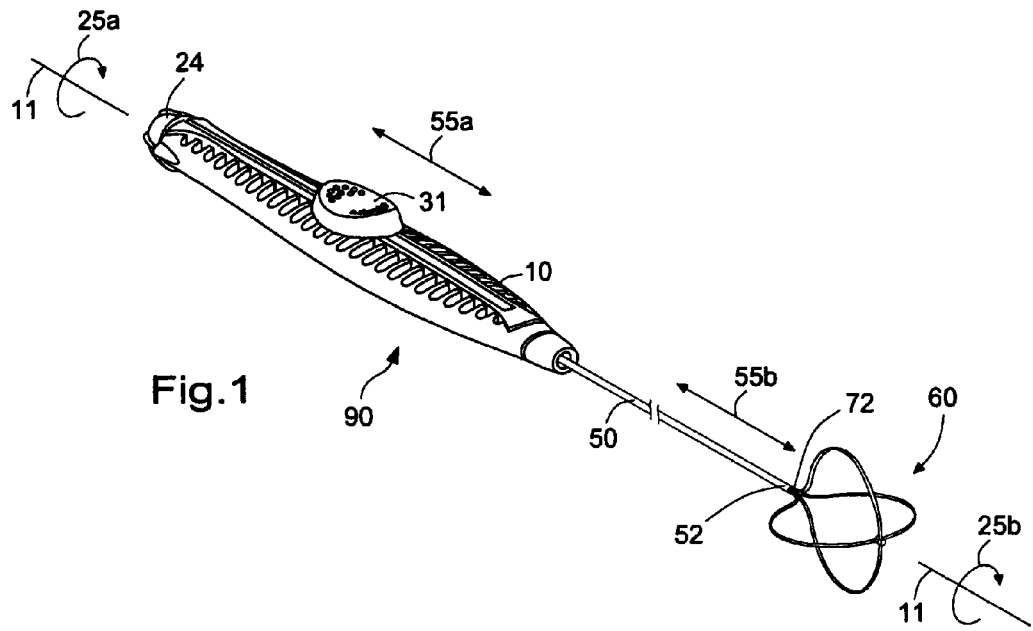
FIG. 1 is an isometric view of an embodiment of the present invention.
Figure 2:
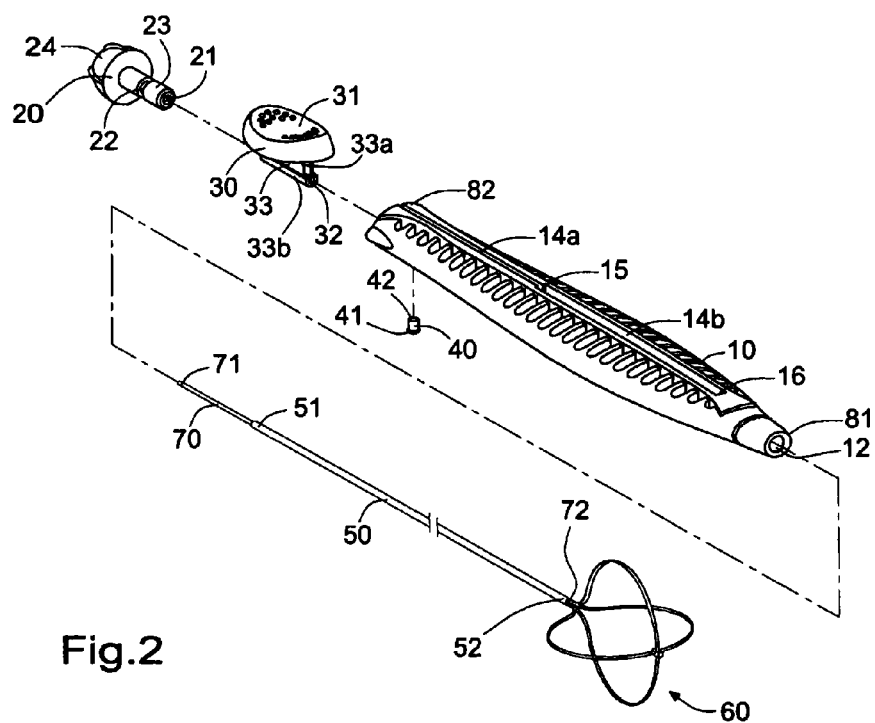
FIG. 2 is an exploded isometric view of FIG. 1.

To operate the device, the user wraps four fingers of one hand partially around handle base 10, but not overlapping thumb pad 31. The tip of the thumb of the same hand is placed on thumb pad 31. Referring to FIGS. 1 and 4, basket 60 is in the open or expanded position. In this position, thumb pad 31 is located at proximal end 15 of wide portion of slot 14b. To actuate the device to the closed or retracted position, the user extends the thumb outward from the hand while maintaining contact between the thumb and thumb pad 31 and keeping handle base 10 stationary in the hand. This action causes thumb slide 30 to slide within wide portion of slot 14b toward distal end 16 of wide portion of slot 14b (arrow 55a). This longitudinal movement of thumb slide 30 relative to handle base 10 propels sheath 50 over drive wire 70 (arrow 55b). This enables longitudinal movement of sheath 50 relative to basket 60, forcing basket 60 to collapse and become enclosed within sheath 50. When thumb slide 30 rests at distal end 16 of wide portion of slot 14b, basket 60 is in the closed or retracted position within sheath 50, as shown in FIGS. 3 and 3a. The distal end of basket 60, including hub 63, may retract completely within sheath 50, or may be sized such that it will not fit within the lumen of sheath 50, but stops adjacent to distal end 52 of sheath 50. In the latter case, the tip configuration and sizing must be such that the device in its fully closed position will pass through the working channel of the endoscope used. If, for example, the object the device is being used to retrieve is a kidney stone located within a calyx of the kidney, the device is introduced in this retracted position through the working channel of an endoscope into the kidney until the retracted basket emerges from the tip of the endoscope in the proximity of the kidney stone. The user then pulls the thumb back toward the hand, sliding thumb pad 31 back toward proximal end 15 of wide portion of slot 14b (arrow 55a). This action pulls sheath 50 back relative to drive wire 70 and basket 60 (arrow 55b). Basket 60 is then exposed and resumes its expanded shape, as shown in FIGS. 1 and 4. At minimum, the actuation means comprise the sheath and drive wire, which are longitudinally movable relative to each other in order to effect opening and closing of the basket.

Handle assembly 90 is then manipulated in order to entrap the object within basket 60. Longitudinal manipulation of basket 60 relative to the object is accomplished by pushing or pulling handle assembly 90 along longitudinal axis 11. Rotational positioning of basket 60 is accomplished by grasping knob 24 of spinner 20 with the thumb and forefinger of the user's second hand, and rotating spinner 20 about longitudinal axis 11 (arrow 25a), relative to handle base 10, which is kept stationary with the first hand. This causes drive wire 70 to rotate within sheath 50, and basket 60 to rotate relative to sheath 50 the same amount in the same direction (arrow 25b). Once the object has been engaged within basket 60, the user then pushes thumb pad 31 forward part way toward distal end 16 of wide portion of slot 14b until basket 60 is partially closed in order to securely hold the object. The device and the endoscope are then simultaneously withdrawn from the patient, holding thumb pad 31 stationary relative to handle base 10 to keep the object secured within basket 60.

Another embodiment of the invention is shown in FIG. 10a. In this embodiment, the basket consists of a hub 83 and four basket wires 81a-81d. Hub 83, which is shown in greater detail in FIGS. 11a and 11b, is in the form of a planar ring that has a distal end 87, a proximal end 88, a longitudinal length LL, a width W and an inside diameter ID. Longitudinal length LL is greater than width W. In preferred embodiments, longitudinal length LL is less than 0.030 inches and width W is less than 0.025 inches. Inside diameter ID provides two ports, 85a and 85b, one on each side of hub 83. Hub 83 is constructed of a rigid material such as stainless steel, nickel titanium alloy, or a material with similar properties; or of a flexible material, such as rubberized thermoplastic, silicone, or a material with similar properties. Hub 83 may be made from hypodermic tubing, or may be formed by machining, extruding, molding, casting or other processes known in the art. In the embodiment shown in FIG. 10a, basket wires 81a and 81b are constructed from a continuous piece of wire, and basket wires 81c and 81d are constructed from a second continuous piece of wire. Hub 83 is oriented so that longitudinal length LL is substantially parallel to the longitudinal axis of the basket. The intersecting area of the basket wires is configured as follows. The continuous wire that forms basket wires 81a and 81b passes into hub 83 through one of ports 85a or 85b and passes out through the other port. Similarly, the continuous wire that forms basket wires 81c and 81d passes into hub 83 through one of ports 85a or 85b and passes out through the other port. The two continuous pieces of wire are positioned so that they are approximately perpendicular to one another, while opposing basket wires 81a and 81b are substantially planar and opposing basket wires 81c and 81d are substantially planar. The radial spacing $S_1$ between two basket wires 81*a* and 81*b* made from the same continuous strand of material is approximately 180°. Hub 83 is positioned at approximately a 45° angle to each of the four basket wires 81*a*-81*d*. Inside diameter ID and ports 85*a* and 85*b* act as hinging means for the basket wires as the basket opens and closes.

Another embodiment is described in FIG. 10*b* that also incorporates the hub shown in FIGS. 11*a* and 11*b*. Basket wires 81*a* and 81*b* are constructed from a continuous piece of wire, and basket wires 81*c* and 81*d* are constructed from a second continuous piece of wire. Hub 83 is oriented so that longitudinal length LL is substantially parallel to the longitudinal axis of the basket. The intersecting area of the basket wires is configured as follows. The continuous wire that forms basket wires 81*a* and 81*b* passes into hub 83 through one of ports 85*a* or 85*b*, bends radially at approximately a 90° angle, and passes out through the other port. Similarly, the continuous wire that forms basket wires 81*c* and 81*d* passes into hub 83 through one of ports 85*a* or 85*b*, bends radially at approximately a 90° angle in the opposite direction from the previous wire, and passes out through the other port. The two continuous pieces of wire are positioned so that the four basket wires 81*a*-81*d* are approximately perpendicular to one another, while opposing basket wires 81*a* and 81*d* are substantially planar and opposing basket wires 81*b* and 81*c* are substantially planar. The radial spacing $S_2$ between two basket wires 81*a* and 81*b* made from the same continuous strand of material is approximately 90°. Hub 83 is positioned at approximately a 45° angle to each of the four basket wires 81*a*-81*d*. Inside diameter ID and ports 85*a* and 85*b* act as hinging means for the basket wires as the basket opens and closes. This embodiment differs from that shown in FIG. 10*a* in that the two basket wires constructed from a continuous piece of wire form adjacent basket wires rather than opposing basket wires.

A variation on the embodiment of FIG. 10*b* is shown in FIG. 10*c*. In this embodiment, the continuous wire that forms basket wires 81*a* and 81*b* passes into hub 83 through one of ports, for example 85*a*, bends radially at approximately a 90° angle, and passes out through the other port, for example 85*b*. The wire then wraps around the outside of hub 83 in the configuration of a fairly tight 360° loop, re-enters port 85*a*, and again passes out through port 85*b*. Thus the total path of the wire is approximately 450°. In a similar fashion, the continuous wire that forms basket wires 81*c* and 81*d* passes into hub 83 through one of ports, for example 85*a*, bends radially at approximately a 90° angle in the opposite direction from the previous wire, and passes out through the other port, for example 85*b*. The wire then wraps around the outside of hub 83 in the configuration of a fairly tight 360° loop, re-enters port 85*a*, and again passes out through port 85*b*. Thus the total path of the wire is approximately 450°. The two continuous pieces of wire are positioned so that the four basket wires 81*a*-81*d* are approximately perpendicular to one another, while opposing basket wires 81*a* and 81*d* are substantially planar and opposing basket wires 81*b* and 81*c* are substantially planar. The radial spacing $S_3$ between two basket wires 81*a* and 81*b* made from the same continuous strand of material is approximately 90°. Hub 83 is positioned at approximately a 45° angle to each of the four basket wires 81*a*-81*d*. The two 360° loops around hub 83 are substantially perpendicular to the longitudinal axis of the basket when the basket is in the open position. This configuration gives greater stability to the basket at its distal end. Inside diameter ID and ports 85*a* and 85*b* act as hinging means for the basket wires as the basket opens and closes.

Yet another variation of the embodiments shown in FIGS. 10*a*-10*c* is described in FIG. 10*d*. In this embodiment, the continuous wire that forms basket wires 81*a* and 81*b* comes from the direction of one of the ports, for example 85*a*, but passes along the outside of hub 83, then bends back approximately 135°, and passes into hub 83 through the other port, for example 85*b*. The wire then exits through the first port, for example 85*a*, then continues to bend approximately 135° further around the outside of hub 83 in for an overall configuration of a fairly tight 270° loop. Thus the continuous piece of wire forms two adjacent basket wires 81*a* and 81*b*, which intersect each other just outside of hub 83 and are approximately perpendicular to each other. In a similar fashion, the continuous wire that forms basket wires 81*c* and 81*d* comes from the direction of one of the ports, for example 85*a*, but passes along the outside of hub 83 opposite to basket wires 81*a* and 81*b*, then bends back approximately 135°, and passes into hub 83 through the other port, for example 85*b*. The wire then exits through the first port, for example 85*a*, then continues to bend approximately 135° further around the outside of hub 83 in for an overall configuration of a fairly tight 270° loop. Thus the continuous piece of wire forms two adjacent basket wires 81*c* and 81*d*, which intersect each other just outside of hub 83 and are approximately perpendicular to each other. The two continuous pieces of wire are positioned so that the four basket wires 81*a*-81*d* are approximately perpendicular to one another, while opposing basket wires 81*a* and 81*d* are substantially planar and opposing basket wires 81*b* and 81*c* are substantially planar. The radial spacing $S_4$ between two basket wires 81*a* and 81*b* made from the same continuous strand of material is approximately 90° or greater. Hub 83 is positioned at approximately a 45° angle to each of the four basket wires 81*a*-81*d*. The two 270° loops around hub 83 are substantially perpendicular to the longitudinal axis of the basket when the basket is in the open position. This configuration also provides stability to the basket at its distal end. Inside diameter ID and ports 85*a* and 85*b* act as hinging means for the basket wires as the basket opens and closes.

Another embodiment of the hub is shown in FIGS. 11*c* and 11*d*. This hub is similar to the hub in described in FIGS. 11*a* and 11*b*, but has a width W that is greater than its longitudinal length LL. It is preferred in this embodiment that width W is greater than 0.025 inches. This elongated hub provides additional strength, which may be beneficial if the hub is constructed of a flexible material. This elongated hub also increases the radial dimensions of the basket intersecting area, which could further reduce trauma to tissue caused by the distal end of the basket.

For all of the embodiments shown in FIGS. 10*a*-10*d* and 11*a*-11*d*, the basket wires could optionally be secured within the hub by means of soldering, welding, crimping, swaging, interference fit, adhesive bonding or other bonding means. If secured within the hub, the basket wires would not need to be constructed from continuous pieces of wire, but rather each basket wire could be formed from a separate piece that terminates within the hub. While these embodiments have been described in the context of four wire baskets, those skilled in the art will appreciate that the hub and basket wire intersecting area concepts described herein could readily be applied to baskets having another number of wires. Hub 83 could also be made in other shapes, and could also be made in a non-continuous ring with a small gap in one place.

Another embodiment of the hub is shown in FIGS. 11*e* and 11*f*. A bilumen hub 183 has a distal end 187, a proximal end 188, a width W, and a longitudinal length LL. Width W may be greater than, less than, or equal to longitudinal length LL. Hub 183 is of a generally cylindrical shape along width W, and distal end 187 and/or proximal end 188 may be flattened, thereby reducing longitudinal length LL. Two lumens or holes 185 and 186 pass completely through hub 183 along width W. The two ends of hole 185 form two ports 185a and 185b, and the two ends of hole 186 form two ports 186a and 186b. Hub 183 may be constructed of a rigid material such as stainless steel, nickel titanium alloy, or a material with similar properties; or of a flexible material, such as rubberized thermoplastic, silicone, or a material with similar properties. Hub 183 may be formed by machining, extruding, molding, casting or other processes known in the art. It will be appreciated that hub 183 could be used for a number of configurations of basket wires, for example, the basket configurations shown in FIGS. 10b, 10c, and 10d, and other basket configurations for which the continuous pieces of wire that form the basket do not intersect within the hub. The basket wires could optionally be secured within hub 183 by means of soldering, welding, crimping, swaging, adhesive bonding or other bonding means. If secured within the hub, the basket wires would not need to be constructed from two continuous pieces of wire, but rather each basket wire could be formed from a separate piece that terminates within hub 183. While hub 183 has been described with two lumens, it could similarly be made with another number, for example three, which could provide a six wire basket, or four lumens, which could be used for an eight wire basket. Alternatively, multiple basket wires could share a single lumen, for example, a two lumen hub could be used for an eight wire basket. This would be particularly useful in the case of a paired wire basket, in which pairs of closely spaced basket wires follow similar paths. Hub 183 could also be made in other shapes, and the lumens could be such that they are not straight or are not parallel with each other.

Another embodiment of the invention is shown in FIG. 12a. In this embodiment, the basket consists of a hub 93 and four basket wires 91a-91d. Hub 93, which is shown in greater detail in FIGS. 12b and 12c, is in the form of a planar ring that has a proximal end 96, a distal end 97, a longitudinal length LL, an inside diameter ID, and an outside diameter OD. Hub 93 has four ports or holes 95a-95d passing through it radially that are spaced approximately 90° to each other. Holes 95a-95d act as receiving means for the basket wires, and may be sized to provide a friction fit, or binding means, to secure the basket wires, or may be sized to allow the wires greater freedom of movement, in which case the holes act as hinging means for the basket wires as the basket opens and closes. Holes 95a-95d are located so that they are substantially in the same plane, which is approximately perpendicular to the longitudinal axis of the basket. Hub 93 is constructed of a rigid material such as stainless steel, nickel titanium alloy, or a material with similar properties; or of a flexible material, such as rubberized thermoplastic, silicone, or a material with similar properties. Hub 93 may be formed by machining, extruding, molding, casting or other processes known in the art. In the embodiment shown in FIG. 12a, basket wires 91a and 91b are constructed from a continuous piece of wire, and basket wires 91c and 91d are constructed from a second continuous piece of wire. Hub 93 is oriented so that longitudinal length LL is substantially parallel to the longitudinal axis of the basket. The continuous wire that forms basket wires 91a and 91b passes into hub 93 through hole 95a, bends radially at approximately a 90° angle, and passes out through hole 95b. Similarly, the continuous wire that forms basket wires 91c and 91d passes into hub 93 through hole 95c, bends radially at approximately a 90° angle in the opposite direction from the previous wire, and passes out through hole 95d. The two continuous pieces of wire are positioned so that the four basket wires 91a-91d are approximately perpendicular to one another, while opposing basket wires 91a and 91d are substantially planar and opposing basket wires 91b and 91c are substantially planar. The radial spacing $S_5$ between two basket wires 91a and 91b made from the same continuous strand of material is approximately 90°. It will be recognized that the hub described in FIGS. 12b and 12c is similar to the hub described in FIGS. 6a and 6b and discussed previously. The main difference is that the four holes 95a-95d in hub 93 are located in substantially the same plane, whereas hub 63 has two opposite holes 65a and 65b that are located closer to distal end 67 of hub 63, and the other two opposite holes 65c and 65d are located closer to proximal end 66 of hub 63. When all of the holes are in the same plane, as in FIGS. 12b and 12c, longitudinal length LL can be smaller than if the holes were in multiple planes. In this embodiment, longitudinal length LL is 0.035 inches or less, but preferably 0.018 inches or less.

Yet another embodiment of the invention is shown in FIGS. 13a-13c. In this embodiment, the basket consists of four basket wires 161a-161d, and a hub 163. In FIG. 13a, the basket is shown in the closed position, substantially retracted into a sheath 152. In this embodiment, opposing basket wires 161a and 161b are formed from a continuous piece of wire, and opposing basket wires 161c and 161d are formed from a second continuous piece of wire. With the basket wires arranged in the desired configuration at their intersecting point, which in this example is spaced approximately 90° apart, hub 163 is formed by applying a hardenable material such as solder, epoxy, or another adhesive or boding agent, which encases the junction of the wires and secures the wires in the desired arrangement. Alternatively, the hub could be made of thermoplastic using an injection molding process such as insert molding. When the hub material hardens, the wires are secured. This material that forms the hub may be substantially flexible, having a shore D hardness of 70 or less, or may be substantially rigid, having a shore D hardness greater than 70. Hub 163 has four ports or holes 165a-165d which are formed necessarily by the presence of basket wires 161a-161d during the application of the hardenable material that forms hub 163. Holes 165a-165d are thus substantially the same shape as and are substantially filled by basket wires 161a-161d, respectively. Alternatively, hub 163 could be formed by welding the basket wires together at their intersecting point, rather than by applying a hardenable material.

FIGS. 14a and 14b show another possible basket configuration according to the invention. This basket has a generally hemispherical shape in the distal portion of the basket and a generally conical shape in the proximal portion of the basket. This basket has a total of eight basket wires, formed from four continuous pieces of wire. The basket wires are positioned so that there are four pairs of closely spaced basket wires, each pair being spaced approximately 90° from the adjacent pairs. The wire intersecting area is similar to the configuration shown in FIGS. 4a and 4b and discussed previously, except that the two wires of each closely spaced pair pass through each hole in the hub, rather than one wire. The paired wires can be advantageous for retaining small stones or stone fragments, and the increased wire mass also increases the strength of the basket.

FIGS. 14c and 14d show another possible basket configuration similar to the basket shown in FIGS. 14a and 14b. The main difference is that this basket has a total of six basket wires, formed from three continuous pieces of wire. Two of the continuous pieces of wire are closely spaced and pass through one hole in the hub and emerge from the hub together through the opposite hole in the hub, forming two pairs of basket wires, spaced approximately 180° from each other. The third continuous wire, which may have different cross-sectional shape and/or dimensions from the other basket wires, passes through one of the remaining holes in the hub and emerges from the opposite hole. The resulting basket consists of four legs, spaced approximately 90° apart. Two opposite legs each consist of a pair of closely spaced wires, while the other two opposite legs each consist of a single wire.

FIGS. 14e and 14f show another possible basket configuration according to the invention. This is a four wire basket that has a hub and basket wire intersecting area that could be made using a number of the different embodiments described herein. The basket wires are formed in a helical shape by means known to those skilled in the art. When viewed from the end of the basket, as in FIG. 14f, the four basket wires appear as four petals spaced approximately 90° apart. Many other embodiments of the invention are also possible. For example, additional basket shapes, different numbers of basket wires, additional materials, different construction of the drive wire, different construction of the sheath, different types and styles of handles, different arrangements of the basket wires at the hub, additional basket wire cross-sections and different sizes, shapes and orientations of the holes or ports in the hub.

The following is one approach to shaping the basket wires when using the hub according to this invention. This example uses nitinol wire for the basket material. First the hub is positioned with the basket wires at the distal intersecting point. The wires are then secured at the proximal end of the basket. Additional securing of the basket wires within the hub can be done, if desired, at this point or after the heating process is complete. The basket wires are then placed in their desired shape either one at a time, in multiples, or all together. A hemispherically shaped form with grooves is used to position all of the basket wires in their proper shape and spacing at the same time. The form also has means to position the hub. Heat is then applied (approximately 400 to 500° C.) to set the basket wire shape. Alternatively, the wires could be preformed, then assembled together with the hub, and then secured at the proximal end of the basket. Additional securing of the distal intersection within the hub, if desired, can be done at any point in the process.

It can be seen from the above description that the medical retrieval device according to this invention has a basket with a distal configuration that permits it to retrieve objects that are positioned in difficult to reach locations, such as kidney stones located in a calyx of the kidney. This distal configuration also serves to reduce trauma to body tissue. It can also be seen that the medical device according to this invention has a mechanism for restricting the degree of relative movement between the basket wires using a separate component, or hub. This hub also provides space between the basket wires at the distal end of the capture space even when the basket is in the closed position, which is particularly helpful in maintaining a grip on small objects such as small stones or stone fragments that might otherwise slip out of the basket as the basket wires are closed. The circular rim of the proximal end of the hub provides many contact points to provide a stable anchor for the distal end of the captured object.

Another aspect of this hub is the plurality of radially disposed holes or ports that stabilize the orientation between the basket wires and add stiffness to the wire section closest to the hub. This is done through the cantilever support that the hub provides to the basket wires. The smaller the holes or openings, the more the cantilever support provided to the wires. Different sized openings and wire cross section configurations can provide more support in one direction and less in another.

Another aspect of this invention is the configuration of the basket wire cross section. We have found it advantageous to have the ratio of width to thickness dimension to be approximately 1.1:1.0 to 1.5:1.0, more specifically in the range of approximately 1.2:1.0 to 1.3:1.0. This provides basket stability when opening or closing the basket. It also provides a preferred direction that the wire would wrap around the stone.

Another aspect of this invention is having a single span of basket wire containing different wire cross sections. For example, the proximal section of the basket could have a cross section with width to thickness dimensions of 4:1, with a mid-section of 2:1 and the distal section of 1:1. Another example would be different shapes in the single span, such as square and round, even if they have the same radial to circumferential dimensions. All these configurations allow for basket designs that optimize the performance to the needs of each section within a basket. Another example would be using a wire that is flattened in the proximal section to maintain circumferential spacing and round in the distal section for bi-directional stability.

A further aspect of this invention is the shortened longitudinal length of the basket wire intersecting area at the distal end of the basket. This invention has longitudinal lengths of approximately 0.040 inches or less but preferably 0.020 inches or less, whereas prior art baskets have longer lengths. This is advantageous in trying to retrieve objects from difficult to reach locations, such as kidney stones located in the calices of the kidney.

Another aspect of the invention is the use of a drive wire that exhibits different flexibilities within the same strand of material by varying the cross-sectional shape or diameter of the wire. This can be done by centerless grinding a tapered section and a smaller diameter straight section in the distal section of the drive wire. Varying the flexibility in a single strand can also be achieved by increasing the depth in a spiral groove at desired locations. This is advantageous because the added flexibility can prevent the distal end of the shaft from limiting the deflection of a flexible endoscope. This can be important when complete deflection of the endoscope is needed for difficult to reach locations, such as the lower poles of the kidney. The many other advantages include smooth transitions between sections with different stiffness, better torque transmission for more precise control of basket rotation, reduced failure modes from joint elimination, and better device actuation without the need for another component to fill the sheath lumen.

Another aspect of this invention is the use of a flattened section (or a reduced radial dimension) in the basket wire at the distal end of the basket. This reduces the amount of strain in the basket wire in an area that receives the most deformation as the basket is retracted into the sheath.

It can also be seen from the above description that the medical retrieval device according to this invention has a mechanism for precisely rotating the basket that is independent of the extension and retraction actuation mechanism used to collapse and expand the basket. This permits rotation of the basket without requiring the user to rotate the entire handle assembly, allowing for improved user comfort. This also permits rotation of the basket without requiring the sheath to rotate within the working channel of the endoscope, thereby allowing more precise control of basket rotation. The handle base isolates the spinner from the thumb slide actuator. This prevents inadvertent longitudinal actuation of the basket during rotation and inadvertent rotation of the basket during longitudinal actuation. It can also be seen that the handle assembly is of a thumb slide actuated type that is comfortable for the user to hold and operate. It can further be seen that the handle uses a minimal number of parts, reducing cost and simplifying assembly. This gives the desirable result of a handle assembly of a preferred style that allows precise and separate control of the actuation and rotation of the basket, and is comfortable for the user to hold and operate.

Another aspect of the invention is the method of manufacturing the medical retrieval device as described above.

The present invention may be embodied in other specific forms without departing from the spirit or essential attributes thereof, and it is, therefore, desired that the present embodiments be considered in all respects as illustrative and not restrictive.

What is claimed is:

1. A medical retrieval device for use in a medical procedure for extraction of a stone, the device comprising:
    a sheath having a proximal end, a distal end, and a lumen defined therebetween;
    a basket formed of a plurality of wires, the basket including:
        a closed configuration wherein the basket is retracted within the lumen of the sheath;
        an open configuration wherein the basket is extended from the lumen of the sheath so as to define an entrapment space therein for entrapping a stone, the open configuration having a proximal portion proximate the sheath and a distal portion having a substantially tipless configuration; and
        at least two of the wires each having a plurality of cross sectional shapes, one of the cross sectional shapes being generally uniform along a first longitudinal portion of the wire and another of the cross sectional shares being generally uniform along a second longitudinal portion of the wire, and each of the cross sectional shapes having a different corresponding thickness, the thickness being a cross sectional dimension of the wire along a line defined perpendicular to the wire and coplanar with a longitudinal axis of the basket; and
    a drive wire which is configured to be movable within the lumen of the sheath, the drive wire connected to the basket at the distal portion such that the drive wire is able to push the basket out of the lumen of the sheath into the open configuration or pull the basket into the lumen of the sheath into the closed configuration.

2. The medical retrieval device of claim 1, wherein the entirety of the basket is not able to be retracted into the lumen of the sheath so that a portion of the basket remains outside the sheath when the basket is in the closed configuration.

3. The medical retrieval device of claim 1, wherein the basket and the sheath are configured such that the entirety of the basket is prevented from being withdrawn into the lumen of the sheath, and such that a portion of the basket remains outside of the sheath when the basket is in the closed configuration.

4. The medical retrieval device of claim 1, wherein an outside diameter of the sheath provides reduced flow resistance to irrigation fluid within a working channel of an endoscope used in conjunction with the medical retrieval device.

5. The medical retrieval device of claim 1, wherein the cross sectional shape of the wires in the distal portion of the basket comprises a flattened shape having a width greater than a thickness.

6. The medical retrieval device of claim 1, wherein the cross sectional shape of the wires in the proximal portion of the basket is configured to enhance stability and radial force of the basket.

7. The medical retrieval device of claim 1, wherein the cross sectional shape of the wires in the distal portion of the basket is configured to provide flexibility for capturing objects.

8. The medical retrieval device of claim 1, wherein the cross sectional shape of the wires in the distal portion of the basket is configured to reduce an amount of stress on the wires when the basket is in the closed configuration.

* * * * *